United States Patent [19]

Ruecroft et al.

[11] Patent Number: 5,663,356

[45] Date of Patent: Sep. 2, 1997

[54] METHOD FOR PREPARATION OF ARYL SUBSTITUTED ALEFINIC SECONDARY AMINO COMPOUNDS

[76] Inventors: Graham Ruecroft, 17, Nuns Orchard, Histon Cambridgeshire CB4 4EW; Martin Woods, 24, Chaucer Road, Royston Hertfordshire SG8 5AP, both of United Kingdom

[21] Appl. No.: 635,165

[22] Filed: Apr. 23, 1996

[51] Int. Cl.$^6$ .................................................. C07D 213/62
[52] U.S. Cl. .......................... 546/300; 546/314; 546/315; 546/329
[58] Field of Search .................................... 546/300, 329, 546/314, 315

[56] References Cited

U.S. PATENT DOCUMENTS 5,212,188  5/1993  Caldwell et al. ........................ 514/343

FOREIGN PATENT DOCUMENTS

WO96/20600  7/1996  WIPO .

OTHER PUBLICATIONS

LaForge, F. B., "The Preparation and Properties of Some New Derivatives of Pyridine", J. Am. Chem. Soc., vol. 50, pp. 2477–2483 (1928).

Acheson, R. M. et al., "Transformations involving the Pyrrolidine Ring of Nictone", J. Chem. Soc., Perking Trans. 1., vol. 2, pp. 579–585 (1980).

Loffler et al., Chem. Ber., vol. 42, pp. 3431–3438 (1909).

Joyce, N. J. et al., "The Formation of 1–Methyl–3–Nicotinoylpyrrolidine from Nicotine–1'–Oxide", Heterocycles, vol. 29, No. 7, pp. 1335–1342 (1989).

Frank, W. C. et al., "Palladium–Catalyzed Vinylic Substitution Reactions with Heterocyclic Bromides", J. Org. Chem., vol. 43, No. 15, pp. 2947–2949 (1978).

Malek, N. J. et al., "Palladium–Catalyzed Synthesis of Cinnamylamines", J. Org. Chem . . . , vol. 47, pp. 5395–5397 (1982).

Sprouse, C. T. et al., "Isomers of metanicotine and the Pinner–Etard reaction", In Abstracts of Papers, Coresta/TCRC, pp. 32–33 (1972).

Cooper, Donald A. et al., "Femtogram On–column Detection of Nicotine by Isotope Dilution Gas Chromatography/Negative Ion Detection Mass Spectrometry", Biological Mass Spectrometry, vol. 22, (1993).

Pinner, A., "Ueber Nicotin (Metanicotin)", Chem. Ber., pp. 1053–1061 (1894).

Pinner, A., "Ueber Nicotin", Chem. Ber., pp. 2861–2870 (1894).

*Primary Examiner*—Amelia Owens

[57] ABSTRACT

Patients susceptible to or suffering from central nervous system are treated by administering an effective amount of an aryl substituted olefinic amine compound, such as (E)-metanicotine. (E)-metanicotine is provided from nicotine. Nicotine is reacted with ethyl chloroformate to produce ethyl N-methyl-N-[4-chloro-4-(3-pyridyl)butyl]carbamate, which then is reacted in the presence of potassium tert-butoxide, tetrahydrofuran and dimethylformamide to produce (E)-metanicotine N-ethyl carbamate, which then is subjected to hydrolysis using hydrochloric acid to produce a reaction mixture containing (E)-metanicotine. The reaction mixture containing (E)-metanicotine is adjusted to a slightly basic pH, and then contacted with dichloromethane. The resulting water immiscible phase then is separated from the aqueous phase. The aqueous phase, then is adjusted to a very basic pH, and then contacted with methyl tert-butyl ether. (E)-metanicotine is taken up by the methyl tert-butyl ether, and after separation of the methyl tert-butyl ether from the aqueous phase, the desired product is separated from the methyl tert-butyl ether.

8 Claims, No Drawings

METHOD FOR PREPARATION OF ARYL SUBSTITUTED ALEFINIC SECONDARY AMINO COMPOUNDS

BACKGROUND OF THE INVENTION

The present invention relates to compounds having pharmaceutical properties, and in particular, to compounds useful for preventing and treating central nervous system (CNS) disorders. The present invention also relates to compositions of matter useful as pharmaceutical compositions in the prevention and treatment of CNS disorders which have been attributed to neurotransmitter system dysfunction. The present invention more particularly relates to a method for providing certain compounds exhibiting nicotinic pharmacology.

CNS disorders are a type of neurological disorder. CNS disorders can be drug induced; can be attributed to genetic predisposition, infection or trauma; or can be of unknown etiology. CNS disorders comprise neuropsychiatric disorders, neurological diseases and mental illnesses; and include neurodegenerative diseases, behavioral disorders, cognitive disorders and cognitive affective disorders. There are several CNS disorders whose clinical manifestations have been attributed to CNS dysfunction (i.e., disorders resulting from inappropriate levels of neurotransmitter release, inappropriate properties of neurotransmitter receptors, and/or inappropriate interaction between neurotransmitters and neurotransmitter receptors). Several CNS disorders can be attributed to a cholinergic deficiency, a dopaminergic deficiency, an adrenergic deficiency and/or a serotonergic deficiency. CNS disorders of relatively common occurrence include presenile dementia (early onset Alzheimer's disease), senile dementia (dementia of the Alzheimer's type), Parkinsonism including Parkinson's disease, Huntington's chorea, tardive dyskinesia, hyperkinesia, mania, attention deficit disorder, anxiety, dyslexia, schizophrenia and Tourette's syndrome.

Nicotine has been proposed to have a number of pharmacological effects. Certain of those effects may be related to effects upon neurotransmitter release. See, for example, Sjak-shie et at., *Brain Res.*, Vol. 624, pp. 295–298 (1993), where neuroprotective effects of nicotine are proposed. Release of acetylcholine and dopamine by neurons upon administration of nicotine has been reported by Rowell et al., *J. Neurochem.*, Vol. 43, pp. 1593–1598 (1984); Rapier et al., *J. Neurochem.*, Vol. 50, pp. 1123–1130 (1988); Sandor et al., *Brain Res.*, Vol. 567, pp. 313–316 (1991) and Vizi, *Br. J. Pharmacol.*, Vol. 47, pp. 765–777 (1973). Release of norepinephrine by neurons upon administration of nicotine has been reported by Hall et al., *Biochem. Pharmacol.*, Vol. 21, pp. 1829–1838 (1972). Release of serotonin by neurons upon administration of nicotine has been reported by Hery et al., *Arch. Int. Pharmacodyn. Ther.*, Vol. 296, pp. 91–97 (1977). Release of glutamate by neurons upon administration of nicotine has been reported by Toth et al., *Neurochem Res.*, Vol. 17, pp. 265–271 (1992). Therefore, it would be desirable to provide a pharmaceutical composition containing an active ingredient having nicotinic pharmacology, which pharmaceutical composition is capable of illiciting neurotransmitter release within a subject in order to prevent or treat a neurological disorder. In addition, nicotine reportedly potentiates the pharmacological behavior of certain pharmaceutical compositions used for the treatment of certain CNS disorders. See, Sanberg et al., *Pharmacol. Biochem. & Behavior*, Vol. 46, pp. 303–307 (1993); Harsing et al., *J. Neurochem.*, Vol. 59, pp. 48–54 (1993) and Hughes, *Proceedings from Intl. Symp. Nic.*, S40 (1994). Furthermore, various other beneficial pharmacological effects of nicotine have been proposed. See, Decina et al., *Biol. Psychiatry*, Vol. 28, pp. 502–508 (1990); Wagner et al., *Pharmacopsychiatry*, Vol. 21, pp. 301–303 (1988); Pomerleau et al., *Addictive Behaviors*, Vol. 9, p. 265 (1984); Onaivi et al., *Life Sci.*, Vol. 54(3), pp. 193–202 (1994) and Hamon, *Trends in Pharmacol. Res.*, Vol. 15, pp. 36–39.

It also has been proposed that nicotine can act directly to elicit the release of acetylcholine in brain tissue, to improve cognitive functions, and to enhance attention. See, Warburton et al., *Cholinergic control of cognitive resources, Neuropsychobiology*, Eds. Mendlewicz, et al., pp 43–46 (1993); Rowell, et al., *J. Neurochem.*, Vol. 43, p. 1593 (1984); Sherwood, *Human Psychopharm.*, Vol. 8, pp. 155–184 (1993); Hodges, et al., *Bio. of Nic.*, Edit. by Lippiello, et al., p. 157 (1991); Sahakian, et al., *Br. J. Psych.*, Vol. 154, p. 797 (1989); and U.S. Pat. No. 4,965,074 to Leeson and U.S. Pat. No. 5,242,935 to Lippiello et al. It also has been proposed that nicotine pharmacology is beneficial in suppressing the symptoms associated with certain disorders. See, Devor et al., *The Lancet*, Vol. 8670, p. 1046 (1989); Jarvik, *British J. of Addiction*, Vol. 86, pp. 571–575 (1991); McConville et al., *Am. J. Psychiatry.*, Vol. 148 (6), pp. 793–794 (1991); Newhouse et al., *Brit. J. Addic.*, Vol. 86, pp. 521–526 (1991); McConville et al., *Biol. Psychiatry*, Vol. 31, pp. 832–840 (1992); Sanberg et al., *Proceedings from Intl. Symp. Nic.*, S39 (1994); Merriam et al., *Psychiatr. Annals*, Vol. 23, pp. 171–178 (1993) and Adler et al., *Biol. Psychiatry*, Vol. 32, pp. 607–616 (1992).

Methods for treating various CNS disorders using (E)-metanicotine-type compounds have been proposed. See, U.S. Pat. No. 5,212,188 to Caldwell et al., Bencherif et al., *Soc. for Neurosci.*, 25th Ann. Mtg. (1995) and Lippiello et al., *Soc. for Neurosci.*, 25th Ann. Mtg. (1995). Methods for the preparation of metanicotine and related compounds have been set forth in Pinner, *Chem. Ber.*, pp. 2861–2370 (1894), Löffler et al., *Chem. Ber.*, Vol. 42, pp. 3431–3438 (1909), Laforge, *J.A.C.S.*, Vol. 50, p. 2477 (1928), Sprouse et al., Abstracts of Papers, p. 32, CORESTA/TCRC Joint Conference (1972), Frank et al., *J. Org. Chem.*, Vol. 43(15), pp. 2947–2949 (1978), Acheson et al., *J. Chem. Soc., Perkin Trans.* 1, Vol. 2, pp. 579–585 (1980), Malek et al., *J. Org. Chem.*, Vol. 47, pp. 5395–5397 (1982), Cooper et al, *Biol. Mass Spectrom.*, Vol. 22, pp. 590–594 (1993) and U.S. patent application Ser. No. 08/364,979, filed Jan. 6, 1995.

It would be beneficial to provide individuals suffering from certain CNS disorders with interruption of the symptoms of those diseases by the administration of a pharmaceutical composition which has nicotinic pharmacology and which has a beneficial effect upon the functioning of the CNS, but which does not provide any significant associated side effects (e.g., increased heart rate and blood pressure) attendant with interaction of that compound with cardiovascular sites. It would be desirable to provide a pharmaceutical composition incorporating a compound which interacts with nicotinic receptors which have the potential to affect the functioning of the CNS, but which does not significantly affect those receptors which have the potential to induce undesirable side effects (e.g., appreciable pressor cardiovascular effects and appreciable activity at skeletal muscle sites). It would be highly desirable to provide a useful method for providing a nicotinic compound useful for the prevention and treatment of a CNS disorder.

SUMMARY OF THE INVENTION

The present invention relates to a method for providing aryl substituted olefinic amine compounds, and most preferably providing aryl substituted olefinic secondary amine compounds. The method involves several steps. A nicotinic compound having an aromatic functionality bonded to a cyclic functionality is subjected to conditions sufficient to open the cyclic functionality. For example, nicotine is reacted with ethyl chloroformate to produce ethyl N-methyl-N-[4-chloro-4-(3-pyridyl)butyl]carbamate. The compound so provided then is reacted within an aprotic solvent (i.e., in a non-aqueous environment) under conditions sufficient to cause dehydrohalogenation of that compound, and hence produce an N-protected aryl substituted olefinic amine compound. For example, ethyl N-methyl-N-[4-chloro-4-(3-pyridyl)butyl]carbamate can undergo a reaction in the presence of potassium tert-butoxide, tetrahydrofuran and dimethylformamide, and hence produce (E)-metanicotine N-ethyl carbamate. The aryl substituted olefinic amine compound so provided then is subjected to conditions sufficient to remove the N-protecting group, and hence provide the desired substituent species on the amine nitrogen of the compound. For example, (E)-metanicotine N-ethyl carbamate is subjected to hydrolysis using concentrated hydrochloric acid, and hence produce a reaction mixture containing (E)-metanicotine. As such, an aryl substituted olefinic secondary amine compound is provided.

The present invention also relates to a method for providing the aryl substituted olefinic secondary amine compounds so provided in a relatively pure form. For example, the reaction mixture containing (E)-metanicotine is adjusted to a slightly basic pH (i.e., a pH of about 8 to about 9, most preferably about 8.2–8.3), and then contacted with a water immiscible organic solvent (e.g., dichloromethane). The resulting water immiscible phase, which contains unwanted organic components, then is separated from the aqueous phase. The aqueous phase, which contains the desired aryl substituted olefinic secondary amine compound, then is adjusted to a very basic pH (i.e., a pH above about 11, preferably to about 13), and then contacted with a water immiscible organic solvent (e.g., methyl tert-butyl ether). The desired aryl substituted olefinic secondary amine compound is taken up by the organic solvent, and after separation of the organic solvent from the aqueous phase, the desired product is separated from the organic solvent.

The pharmaceutical compositions incorporating compounds synthesized in accordance with the method of the present invention are useful for the prevention and treatment of CNS disorders. The pharmaceutical compositions provide therapeutic benefit to individuals suffering from certain CNS disorders and exhibiting clinical manifestations of such disorders in that the compounds within those compositions have the potential to (i) exhibit nicotinic pharmacology and affect nicotinic receptors sites in the CNS (e.g., act as a pharmacological agonist to activate nicotinic receptors), and (ii) elicit neurotransmitter secretion, and hence prevent and suppress the symptoms associated with those diseases. In addition, the compounds are expected to have the potential to (i) increase the number of nicotinic cholinergic receptors of the brain of the patient, (ii) exhibit neuroprotective effects and (iii) not provide appreciable adverse side effects (e.g., significant increases in blood pressure and heart rate, and significant effects upon skeletal muscle). The pharmaceutical compositions of the present invention are believed to be safe and effective with regards to prevention and treatment of CNS disorders.

DETAILED DESCRIPTION OF THE PREFERRED EMBODIMENTS

Representative compounds which can be manufactured using the process of the present invention have the formula:

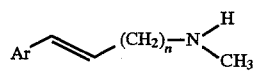

where Ar is an aromatic functionality, such as a pyridine functionality, and n is 1, 2, 3 or 4. Of particular interest, are compounds which have the formula:

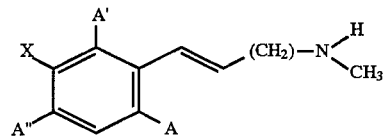

where X is a suitable substituent species characterized as having a sigma m value greater than 0, often greater than 0.1, generally greater than 0.2 and even greater than 0.3; less than 0 and generally less than −0.1; or 0; as determined in accordance with Hansch et al., Chem. Rev., Vol. 91, pp. 165–195 (1991); and n is 1, 2, 3 or 4, preferably 2 or 3, and most preferably is 2; A, A' and A" individually represent hydrogen, alkyl (e.g., lower straight chain or branched alkyl, including $C_1$–$C_7$, but preferably methyl or ethyl) or halo (e.g., F, Cl, Br or I); X includes a substituent species such as —H, —F, —Cl, —Br, —I, —$CF_3$, —$N_3$, —OR', —$C_2$R' and —C(O)R', where R' is hydrogen or lower alkyl (e.g., alkyl containing one to five carbon atoms, preferably methyl or ethyl). In addition, it is highly preferred that A is hydrogen, it is preferred that A' is hydrogen, and normally A" is hydrogen. Generally, both A and A' are hydrogen; sometimes A and A' are hydrogen, and A" is methyl or ethyl; and often A, A' and A" are all hydrogen. One representative compound is (E)-metanicotine, for which n is 2, and X, A, A' and A" each are hydrogen. Another representative compound is 2-methylmetanicotine, for which n is 2, A is methyl, and X, A' and A" each are hydrogen. Another representative compound is 5-bromometanicotine, for which n is 2, X is Br, and A, A' and A" each are hydrogen. It is also possible for certain hydrogen atoms of the olefinic side chain functionality of the compounds to be substituted with a species, such as an alkyl substituent (i.e., lower alkyl, such as methyl or ethyl); and a representative compound of such a type is N-methyl-4-(3-pyridinyl)-1-methyl-3-buten-1-amine.

Representative nicotinic compounds which can be used in carrying out the method of the present invention can vary. Suitable nicotinic compounds are those compounds that have an aromatic functionality bonded to a cyclic functionality that can undergo a ring opening reaction. Representative cyclic functionalities include azetidinyl, pyrollidinyl, piperidinyl and piperazinyl functionalities, preferably pyrollidinyl and piperidinyl functionalities. Representative nicotinic compounds include nicotine, 2-methylnicotine, 5'-methylnicotine, N-methyl anabasine and 2-isonicotine.

The reagent used to provide the ring opening of the nicotinic compound can vary. Representative reagents are set forth in Acheson et al., J. Chem. Soc., Perkin Trans. 1, Vol. 2, pp. 579–585 (1980). The most appropriate reagents are ethyl chloroformate and phenyl chloroformate. Sufficient amount of reagent is used to provide acceptable yield of ring opened compound. For example, a stoichiometric amount of ethyl chloroformate is used to provide ring opened compound at a yield in excess of 95 percent. The ring opening reaction most preferably is conducted in an aprotic environment (i.e., within a nonaqueous solvent, such as tetrahydrofuran or dichloromethane). Although the total absence of water is not crucial, anhydrous conditions are preferred, using aprotic, low boiling point solvents. An aprotic solvent, such as tetrahydrofuran, is preferred because the later dehydrohalogenation can be carried out directly on the nicotinic ring opened compound. Typically, the temperature of the reaction mixture remains below 50° C., and preferably does not exceed about 35° C., and preferably does not exceed about 30° C. As an example of the ring opening reaction of a nicotinic compound, nicotine is reacted with ethyl chloroformate to produce ethyl N-methyl-N-[4-chloro-4-(3-pyridyl)butyl]carbonate.

A C—C double bond is introduced into the ring opened compound, preferably as a result of a dehydrohalogenation reaction of the ring opened compound, using thermal or base catalysis techniques. However, base catalysis is preferred, in order to carry out the synthesis steps at relatively low temperatures. An example of such a reaction involves conversion of ethyl N-methyl-N-[4-chloro-4-(3-pyridyl)butyl] carbamate to (E)-metanicotine N-ethyl carbamate. A preferred catalyst for such a reaction is a catalyst that is effective in an aprotic environment. A particularly preferred catalyst is potassium tert-butoxide. Although the total absence of water is not crucial, it is preferred to employ anhydrous conditions using aprotic, low boiling point solvents. An aprotic solvent, such as tetrahydrofuran, is preferred because contact of a water immiscible solvent, such as t-butyl methyl ether, with water allows for an effective procedure for product isolation. Typically, the temperature of the reaction mixture does not exceed the boiling point of the solvent (e.g., tetrahydrofuran or tetrahydrofuran augmented with dimethylformamide). Preferably, the temperature of the reaction mixture does not exceed about 80° C., and preferably does not exceed about 75° C. Examples of suitable solvents are tetrahydrofuran, and mixtures of solvents such as about 80 to about 90 weight parts tetrahydrofuran and about 10 to about 20 weight parts dimethylformamide. As such, a ring opened compound having a C—C double bond is produced at greater than about 50 percent yield, and under the conditions of reflux (i.e., at about 70° C., such that reformation of nicotine is minimized).

The ring opened compound having a C—C double bond is subjected to hydrolysis to produce the desired compound. Hydrolysis conditions involve heating the ring opened compound with a strong mineral acid, such as concentrated hydrochloric acid, at least about 100° C. Prior to hydrolysis, the ring opened compound can be provided in a relatively pure and clean (i.e., above 80 percent purity, because some nicotine still may be present) form, using distillation techniques, such as falling film or wipe-film distillation techniques.

The compounds of the present invention are provided in a purified form. One method involves adjusting the reaction mixture containing the product compound to a slightly basic pH (i.e., a pH of about 8.2–8.3). The basified aqueous mixture then is contacted with an immiscible organic solvent, such as dichloromethane or methyl tert-butyl ether. The aqueous phase then is basified further to a pH of above about 11. See, Fujita, *Pesticide Biochem and Physiology*, Vol. 1(2), p. 151 (1971). The aqueous phase then is contacted with a second water immiscible organic solvent, such as methyl tert-butyl ether, in order to collect the product compound from the aqueous phase. Another second organic solvent suitable for isolating the product compound is dichloromethane. The second organic solvent then is removed, preferably by evaporation, to provide pure product compound.

The compounds synthesized in accordance with the method of the present invention can be employed in a free base form or in a salt form (e.g., as pharmaceutically acceptable salts, such as chloride, perchlorate, ascorbate, sulfate, tartrate, fumarate, citrate, malate, lactate or aspartate salts). One method for providing the compound in salt form is set forth in of U.S. patent application Ser. No. 08/364,979, filed Jan. 6, 1996. Another method for providing the compound in a fumaric salt form involves (i) adding a solution of suitably pure compound dissolved in tetrahydrofuran to a refluxing solution of fumaric acid in a tetrahydrofuran/ ethanol co-solvent mixture to form a precipitate, (ii) applying heat and additional ethanol to the mixture to dissolve the precipitate, (iii) cooling the resulting solution, and seeding the solution if necessary, to cause precipitation of salt, and (iv) filtering and collecting the salt.

There are advantages of the method of the present invention. The invention provides an effective two component solvent system for the preparation of (E)-metanicotine ethyl carbamate; that is, a solvent mixture of tetrahydrofuran and dimethylformamide. The solvent system and the base catalyst provide (E)-metanicotine ethyl carbamate at good yield (i.e., about 65 to about 75 percent, based on starting nicotinic compound) involving two, relatively low temperature, reactions. In addition, simple hydrolysis of the (E)-metanicotine ethyl carbamate, and the selective extraction of product from by-products, allows for good yield of relatively pure product. Typically, (E)-metanicotine product is obtained at about 30 to about 40 percent yield, based on nicotinic on starting material, and at greater than 90 percent purity.

Compounds provided in accordance with the method of the present invention are useful for providing prevention of a CNS disorder to a subject susceptible to such a disorder, and for providing treatment to a subject suffering from a CNS disorder. In particular, there can be administered to a patient an amount of a compound effective for providing some degree of prevention of the progression of the CNS disorder (i.e., provide protective effects), amelioration of the symptoms of the CNS disorder, and amelioration of the reoccurrence of the CNS disorder. CNS disorders which can be treated by the compounds include presenile dementia (early onset Alzheimer's disease), senile dementia (dementia of the Alzheimer's type), Parkinsonism including Parkinson's disease, Huntington's chorea, tardive dyskinesia, hyperkinesia, mania, attention deficit disorder, anxiety, dyslexia, schizophrenia and Tourette's syndrome.

The following example is provided in order to further illustrate various embodiments of the invention but should not be construed as limiting the scope thereof. Unless otherwise noted, all parts and percentages are by weight.

EXAMPLE (E)-metanicotine monofumarate is provided generally using the following techniques:

Tetrahydrofuran (THF) (4 L) and N,N-dimethylformamide (1.2 L) are charged to a nitrogen purged reaction vessel being rinsed wit)-nicotine (1 kg), the nicotine being rinsed with a further portion of THF (0.85 L). Ethyl chloroformate (0.73 kg) is added slowly to the reaction vessel by dropping funnel, with cooling, keeping the temperature of the reaction mixture in the range of 30°–35° C. When addition is complete, the reaction mixture, which contains ethyl N-methyl-N-[4-chloro-4-(3-pyridyl)butyl] carbamate, is heated slowly to reflux. A solution of potassium tert-butoxide (500 g) in tetrahydrofuran (3 L) is prepared and added dropwise to the reaction vessel while maintaining reflux at, that is about 72° C. Further aliquots of potassium tert-butoxide in tetrahydrofuran are added dropwise until reaction is complete, and typically a total amount of about 690 g of potassium tert-butoxide is employed to complete the reaction. Water (3 L) is added to the cooled reaction mixture, followed by methyl tert-butyl ether (MTBE) (3 L) and the mixture is stirred. The lower aqueous extract is removed and the organic layer is washed with water (3 L). The organic extract is concentrated in vacuo at 50° C. initially, and then at 70° C. to remove all solvents to give the crude (E)-metanicotine N-ethyl carbamate product as a dark brown mobile oil (yield, 1 kg, 69.3%).

Crude (E)-metanicotine N-ethyl carbamate (1.09 kg) from different lots is distilled using a CD-6 Wipe-Film Evaporator operating at 150° C. with a vacuum of 1/100 to 1/1,000 mBar. The rates of substrate addition and rotor speed are adjusted to give a suitable distillation rate. The distilled product is obtained as a yellow to orange oil (0.75 kg). Further purification of the distilled product is conducted by a cool pass run of the product, and the further purified (E)-metanicotine N-ethyl carbamate product is collected at the wipe film evaporator residue port.

Crude distilled (E)-metanicotine N-ethyl carbamate (1.5 kg) from different lots is suspended in water (1 L), and concentrated (32%) hydrochloric acid (4.8 L) is added slowly with stirring. Then, the resulting mixture is refluxed for 17 hrs. The resulting solution is cooled and basified to pH 8.2–8.3 by careful addition of concentrated (32%) sodium hydroxide solution (2.4 L). Dichloromethane (DCM) (2.75 L) is added to the reaction mixture, with vigorous stirring. The lower organic phase of the mixture is separated to waste, and the aqueous layer is similarly re-extracted with further aliquots of DCM (5×2.75 L), which also are separated to waste. The aqueous phase is further basified to pH 13 by the addition of concentrated (32%) sodium hydroxide solution (1.4 L), and MTBE (1.7 L) is added to that aqueous phase. The mixture is separated and the upper organic phase is retained. The aqueous layer re-extracted with MTBE (7×1.7 L). The combined MTBE extracts are concentrated in vacuo, to yield (E)-metanicotine as a clear yellow to brown oil (0.6 kg, 56.9% based on (E)-metanicotine N-ethyl carbamate).

Fumaric acid (419 g) is charged to a reaction vessel and THF (3.19 L) is added. Toluene denatured ethanol (0.72 L) is added, and the mixture is heated and refluxed to 65° C. to dissolve the fumaric acid. (E)-metanicotine (0.585 kg) is dispersed in THF (1.19 L), and the resulting solution is charged into an addition funnel. When the fumaric acid is fully dissolved, the metanicotine solution is added dropwise to the fumaric acid solution. Reflux is maintained throughout addition, and upon completion of addition a cloudy precipitate forms. Toluene denatured ethanol (1.3 L) is added dropwise until a clear solution forms. The solution is cooled slowly to 40° C. When crystallization is established, the vessel is cooled slowly to ambient temperature, and then further cooled to less than 5° C. The slurry is stirred at less than 5° C. for 1 hr., and the product, (E)-metanicotine monofumarate, is collected by filtration. The product filter cake is washed with ice cold THF/toluene denatured ethanol (9:1, 2 L). The filter cake then is slurried on the filter with THF (2×1 L). The (E)-methanicotine monofumarate product is dried in vacuo at 40° C. to constant weight and stored, under nitrogen, in amber jars (706 g, 70.3%).

What is claimed is:

1. A method for providing an aryl substituted olefinic secondary amine compound, the method comprising the steps of:

a) subjecting a nicotinic compound having an aromatic functionality bonded to a cyclic functionality to conditions sufficient to open the cyclic functionality thereby providing a ring opened compound;

b) reacting the ring opened compound within an aprotic solvent and potassium tert-butoxide under conditions sufficient to produce an aryl substituted olefinic amine compound;

c) subjecting the aryl substituted olefinic amine compound so provided to contact with acid and conditions sufficient to provide an aryl substituted olefinic secondary amine within a reaction mixture;

d) adjusting the reaction mixture to a pH of about 8 to about 9, and then contacting that mixture with a water immiscible organic solvent, and then separating water immiscible phase from aqueous phase;

e) subjecting the aqueous phase to a pH above about 11, and then contacting that phase with a water immiscible organic solvent;

f) separating of water immiscible phase from aqueous phase, and collecting the water immiscible phase incorporating organic solvent and aryl substituted olefinic secondary amine compound; and g) separating organic solvent from aryl substituted olefinic secondary amine compound.

2. The method of claim 1 whereby cause dehydrohalogenation of that compound, and thereby step a) is performed in the presence of ethylchloroformate, and step b) is performed to cause dehydrohalogenation of ring opened compound.

3. The method of claim 2 whereby in step d), the pH of the mixture is adjusted to 8.2–8.3.

4. The method of claim 1 whereby step a) and step b) each are carried out at a temperature below 35° C. and 75° C., respectively.

5. The method of claim 1 whereby the nicotinic compound of step a) is nicotine and the aryl substituted olefinic secondary amine compound is (E)-metanicotine.

6. The method of claim 1 whereby the aprotic solvent of step b) includes tetrahydrofuran.

7. The method of claim 6 whereby the aprotic solvent of step b) includes dimethylformamide.

8. The method of claim 1, wherein the nicotinic compound is nicotine and the aryl substituted olefinic secondary amine compound is 5-bromometanicotine.

* * * * *